United States Patent
Ansari et al.

(10) Patent No.: US 9,950,095 B2
(45) Date of Patent: Apr. 24, 2018

(54) IMPLANT AND METHOD OF PRODUCING AN IMPLANT

(71) Applicant: VIDEREGEN LIMITED, Liverpool (GB)

(72) Inventors: Tahera Iqbal Ansari, Harrow (GB); Paul David Sibbons, Harrow (GB)

(73) Assignee: Videregen Limited, Liverpool (GB)

( * ) Notice: Subject to any disclaimer, the term of this patent is extended or adjusted under 35 U.S.C. 154(b) by 0 days.

(21) Appl. No.: 14/892,529

(22) PCT Filed: Jun. 16, 2014

(86) PCT No.: PCT/GB2014/051845
§ 371 (c)(1),
(2) Date: Nov. 19, 2015

(87) PCT Pub. No.: WO2014/202958
PCT Pub. Date: Dec. 24, 2014

(65) Prior Publication Data
US 2016/0095956 A1     Apr. 7, 2016

(30) Foreign Application Priority Data
Jun. 17, 2013 (GB) .................................. 1310773.5

(51) Int. Cl.
*A61L 27/36* (2006.01)

(52) U.S. Cl.
CPC ......... *A61L 27/3683* (2013.01); *A61L 27/365* (2013.01); *A61L 27/3654* (2013.01); *A61L 27/3662* (2013.01); *A61L 27/3687* (2013.01); *A61L 27/3691* (2013.01); *A61L 2430/02* (2013.01)

(58) Field of Classification Search
None
See application file for complete search history.

(56) References Cited

U.S. PATENT DOCUMENTS

2013/0337560 A1* 12/2013 Ross .................... C12N 5/0654
435/366

FOREIGN PATENT DOCUMENTS

WO    WO 11/0620621    *   5/2011    ............... C12Q 1/00

OTHER PUBLICATIONS

Zang et al, "Decellularized Tracheal Matrix Scaffold for Tissue Engineering" Plastic and Reconstructive Surgery, 2012, vol. 130, pp. 532-540. (Year: 2012).*

* cited by examiner

*Primary Examiner* — Allison M Fox
(74) *Attorney, Agent, or Firm* — Notaro, Michalos & Zaccaria P.C.

(57) ABSTRACT

The invention provides a method for producing an implant from interstitial, connective or supporting tissue, the method comprising at least one step of perfusing the tissue with at least one decellularization medium under negative pressure applied for substantially the whole time period of the perfusion.

14 Claims, 12 Drawing Sheets

IMPLANT AND METHOD OF PRODUCING AN IMPLANT

TECHNICAL FIELD OF THE INVENTION

The present invention relates to an implant and a method of producing an implant. The invention is particularly useful in the production of implants derived from cartilaginous or calcified tissues, such as trachea, tendon and bone.

BACKGROUND TO THE INVENTION

Implants comprising biologically derived scaffolds have become important options for tissue/organ repair and regeneration in the treatment of various different diseases and conditions. A continuing and major hurdle is the need to remove antigen-presenting cellular material from the tissue, which tissue then becomes the scaffold. In particular when relatively dense interstitial, connective or supporting tissue, including cartilaginous tissue, such as tracheal tissue, is decellularised, it is very difficult, if not impossible, to remove substantially all antigen-presenting cells from the tissue.

Interstitial, connective and supporting tissue damage, including long tracheal lesions, still represent a challenge to the surgeon. For example, damage resulting from congenital defects, trauma or tumour that compromise more than 4.5-6 cm or more than 30% of the total tracheal length in children is not treatable via primary closure. Thus these patients are rarely considered as surgically curable and the use of implants derived from tracheal tissue is a desired alternative. Reconstruction with a tracheal conduit would extend surgical indications and improve quality of life.

Recent advances in the field of regenerative medicine hold significant promise especially, with regards to tissue engineered replacement tracheal scaffolds. The ideal replacement should be as close to the natural structure as possible providing stability and non-immunogenic characteristics. To fulfil these criteria significant research resources are being directed towards using biological material as a starting point. Preparing a scaffold for regenerative purpose using either allogenic or xenogenic material requires the complete removal of all antigenicity whilst preserving the extracellular matrix to an extent that it is able to support cell attachment and to provide sufficient rigidity for air ventilation.

Known decellularisation techniques use different chemical and biological reagents to wash out antigen presenting cells and cell particles. One established protocol to decellularise tracheal tissue is based on a detergent-enzymatic-method, in which cells are removed from the tracheal tissue by perfusion with various detergents, enzymes and other reagents. Whilst providing a suitable scaffold that had been successfully transplanted in a handful of cases on compassionate grounds, it has not yet reached standard clinical practice. One reason is the lengthy preparation of the scaffold which takes approximately 3 weeks, and the accompanying risk to the patient caused by the time delay.

A standardized "off-the-shelf" scaffold for clinical use requires not only the correct anatomical, functional and biomechanical characteristics but also the feasibility to be prepared in a suitable time frame. To improve decellularisation of tissues, different methods are available, encompassing different combinations of enzymes and detergents. Since the majority of these reagents are known to alter the extracellular matrix a different approach to known techniques is still desired in order to mitigate or prevent alteration of the extracellular matrix.

As interstitial, connective and supporting tissue, such as cartilage, is a specifically dense tissue, a method is required to deliver the decellularising agents deep into the tissue over a relatively short time and with no impact on the tissue ultrastructure of extra cellular matrix, especially when preparing tracheal implants.

The present invention therefore provides an improved method for producing an implant for tissue/organ repair, especially based on interstitial, connective or supporting tissue, including cartilaginous tissue such as the trachea, in which the implant can be prepared in a relatively short period of time, whilst maintaining a substantially intact extra-cellular matrix with removal of substantially all antigen-presenting cells.

SUMMARY OF THE INVENTION

According to a first aspect of the invention there is provided a method for producing an implant from tissue, the method comprising the step of perfusing the tissue with at least one decellularisation medium under negative pressure applied for substantially the whole time period of the perfusion.

According to a second aspect of the invention there is provided a method for producing an implant from interstitial, connective or supporting tissue, the method comprising the step of perfusing the tissue with at least one decellularisation medium under negative pressure applied for substantially the whole time period of the perfusion.

Suitable interstitial, connective or supporting tissues include cartilaginous, fibrocartilaginous and calcified cartilaginous tissue, such as the trachea, larynx and cartilage per se, bone, tendon, ligament, bone-tendon, bone-ligament, nervous tissue, large blood vessels such as arteries and veins, and synovial membrane.

Non-interstitial, connective or supporting tissue that may be used with the methods of the invention include brain, oesophagus, bowel (small and large), pancreas, spleen, liver, lungs, kidney, lymphatics, small blood vessels.

"Negative pressure" includes pressure reduced from ambient, or a partial or substantially complete vacuum.

The resulting scaffold provides an excellent implant for the repair and regeneration of tissue.

The decellularisation process may comprise, in addition to the decellularisation medium perfusion step(s), one or more washing steps. Preferably the or each washing step is also performed under negative pressure for substantially the whole time period of the or each washing step.

In some embodiments substantially the entire implant production method is performed under negative pressure.

The decellularising media are selected so as to deplete cells and cellular components from the tissue whilst minimising damage to the extracellular matrix (ECM) proteins, resulting in a scaffold in which ECM structure and function are preserved as far as possible.

Suitable decellularisation media include detergents, such as sodium dodecyl sulphate (SDS), sodium deoxycholate (SOC), detergents comprising hydrophilic polyoxyethylene-oxide and hydrophobic hydrocarbon moieties, such as Triton X-100®, enzymes, such as proteolytic enzymes, for example trypsin, and nucleases, for example deoxyribonucleases such as DNase I and ribonucleases such as RNase, and combinations thereof. Trisbutyl-n-phosphate (TBnP) may also be included in one or more decellularisation media.

TBnP is a solvent that disrupts protein-protein interactions.

The method preferably comprises perfusing the tissue with more than one decellularising media. Suitably, the method comprises perfusing the tissue with at least one detergent and at least one nuclease. In some embodiments the method comprises separate steps of perfusing the tissue with a detergent and perfusing the tissue with a nuclease, and the detergent perfusion step may be performed before the nuclease perfusion step. In some embodiments each detergent perfusion step is performed under negative pressure, while in some other embodiments both the detergent perfusion and nuclease perfusion steps are performed under negative pressure.

Each perfusion step may be performed at a temperature of between 15° C. and 45° C., or between 30° C. and 40° C. In some embodiments the perfusion steps are performed at around 37° C., which is especially advantageous when the perfusion step includes a nuclease material. When the perfusion step is a detergent perfusion step it may be performed at a temperature of between 15° C. and 40° C. such as around ambient or room temperature.

In some embodiments the method may comprise a washing step between each perfusion step. The washing step may use any suitable washing medium or media, such as phosphate buffered saline (PBS), Hanks balanced salt solution, or sterile water, for example. The washing step(s) may be performed at a temperature of between 1° C. and 8° C., or between 2° C. and 6° C. Alternatively the or each washing step may be performed at a temperature of between 15° C. and 40° C., such as around 37° C., or around ambient or room temperature. Each washing step performed between perfusion steps may be performed under negative pressure and in some embodiments all of the washing steps are performed under negative pressure. A washing step may comprise incubating the tissue in the washing media.

Perfusion and/or washing may be carried out in the presence of antibiotics and/or antimycotics.

The method may comprise perfusing the tissue in a series of steps comprising: at least two steps of perfusion with a nuclease, followed by at least one step of perfusion with a detergent or mixture of detergent, washed in between each step with a washing medium. In some embodiments the series of steps comprises, two steps of perfusion with a mixture of deoxyribonuclease and ribonuclease followed by perfusion with a mixture of ionic and non-ionic detergents, washed in between each step with a saline solution. In preferred embodiments the mixture of detergents comprises sodium deoxycholate and Triton X-100®, the deoxyribonuclease is DNAse I, and the ribonuclease is RNAse.

Suitably each perfusion step is carried out for between 1 hour and 96 hours, more preferably for between 18 hours and 84 hours, and most preferably for between 24 hours and 72 hours. When the perfusion step comprises perfusion of a detergent material the step may be carried out for at least 12 hours, 18 hours or 24 hours. When the perfusion step comprises perfusion of a nuclease, the step may be carried out for at least 1 hour, 18 hours or 24 hours.

Suitably each washing step may be carried out for between 15 minutes and 96 hours such as between 12 hours and 96 hours, more preferably for between 18 hours and 72 hours, or for between 24 hours and 72 hours. There may be multiple washing steps between or after each perfusion step and each of the multiple washing steps may be carried out independently for between 15 minutes and 96 hours.

The method may comprise storing the decellularised tissue in a suitable medium, such as a saline solution. The saline solution may include at least one antibiotic and/or antimycotic material. The saline solution may comprise a phosphate-buffered saline (PBS) solution or Hanks balanced salt solution (optionally with acid Ca and/or Mg) and may comprise both an antibiotic and antimycotic material. Storage is preferably at a temperature of between 1° C. and 6°, such as around 4° C.

The perfusion step or steps are performed under negative pressure. For methods involving interstitial, connective or supporting tissue, the pressure is preferably no more than 10 kPa, 5 kPa, 2 kPa, 1 kPa or 0.5 kPa, at ambient temperature. In some embodiments the pressure is no more than 1 kPa, no more than 0.2 kPa or no more than 0.1 kPa. It is believed that perfusing the tissue with decellularisation agents under such reduced pressure not only increases the speed at which the tissue takes up the perfusion solution and decellularising medium (or media), but also enables the decellularising medium (media) to penetrate deeper into the tissue than would otherwise occur without the use the negative pressure, therefore ensuring that all of the tissue is perfused with the medium (media), in order to enable substantially complete decellularisation in a relatively short time period. In addition, when washing steps are performed under negative pressure, the decellularising effects are maintained and enhanced. For methods involving tissues other than interstitial, connective or supporting tissue (for example oesophagus, bowel, liver, pancreas, kidney, spleen, lungs and small blood vessels), the pressure may be no more than 80 kPa, 70 kPa, 60 kPa, 50 kPa, 40 kPa, 30 kPa, 20 kPa, 10 kPa, 5 kPa, 2 kPa or 1 kPa. In general the pressure for non-interstitial, connective or supporting tissue will be higher than for interstitial, connective or supporting tissue.

In some embodiments the method comprises the steps of:
a) Perfusing the tissue with a nuclease medium for between 1 hour and 36 hours;
b) Washing the tissue for between 12 hours and 72 hours;
c) Perfusing the tissue with a detergent medium for between 12 hours and 36 hours; and
d) Perfusing the tissue with a nuclease medium for a further 12 to 36 hours.

The tissue may be interstitial, connective or supporting tissue as described hereinabove, or non-interstitial, connective or supporting tissue as described hereinabove.

The nuclease medium in steps a) and d) is preferably the same nuclease medium and may comprise DNAse I and RNAse.

The detergent medium in step c) may comprise a mixture of non-ionic and ionic detergents, such as a mixture of sodium deoxycholate and Triton X-100® for example.

The perfusion steps a), c) and d) may be performed at between 30° C. and 40° C., such as around 37° C. The washing steps may be performed at between 2° C. and 6° C., such as around 4° C., or at between 15° C. and 40° C., such as around 37° C., or around ambient or room temperature.

There may be a step e), after step d), of storing the decellularised tissue in a saline solution at between 1° C. and 6° C., such as around 4° C. The saline solution may include an antibiotic and/or an antimycotic.

Steps a), c) and d) are all performed under negative pressure, which may be no more than 10 kPa, 5 kPa, 2 kPa, 1 kPa or 0.5 kPa, at ambient temperature, and preferably no more than 0.2 kPa or more preferably no more than 0.1 kPa for interstitial, connective or supporting tissue, or no more than 80 kPa, 50 kPa, 30 kPa or 10 kPa for any other suitable tissue.

Each of steps a) to d) are preferably performed under negative pressure, which may be no more than 10 kPa, 5 kPa, 2 kPa, 1 kPa or 0.5 kPa, at ambient temperature, and preferably no more than 0.2 kPa or more preferably no more than 0.1 kPa, for interstitial, connective or supporting tissue, or no more than 80 kPa, 50 kPa, 30 kPa or 10 kPa for any other suitable tissue.

There may be other washing steps of between 15 minutes and 72 hours, between any of steps a) to d) and/or after step d).

Optionally, the method of the first or second aspect of the invention may comprise a step of crosslinking the processed tissue. Any suitable crosslinking agent may be used, for example one or more of hexamethylene diisocyanate (HMDI), genipin, quercetin or heparin. Typically, where the method includes a step of crosslinking this is carried out after decellularisation of the tissue.

Cross-linking is particularly advantageous where the implant is produced from trachea as it helps to protect against tracheomalacia.

The method may be used to provide a substantially decellularised scaffold in which cells are substantially removed, the scaffold having removed sufficient cellular material and associated components such that no adverse tissue reactivity or immune reaction is observed in vivo. Reactivity may be observed by subcutaneous implantation. The substantially decellularised scaffold is suitably free from cells as visualised by microscopy ×40 magnification.

When cartilaginous tissue is used, the method of the invention results in decellularisation of the cartilaginous tissue such that substantially all chondrocytes within the lacunae are removed. In addition, when the cartilaginous material is a trachea, substantially all of the nuclei within the luminal epithelium (mucosa), sub-mucosal glands, trachealis muscle and outer adventitia are removed.

In a recent review of tissue and whole organ decellularisation processes (Crapo et al. (2011) *Biomaterials* 32: 3233-3243) it was proposed that the following minimal criteria, in addition to the lack of adverse in-vivo response, suffice to satisfy the intent of extracellular matrix (ECM) decellularisation: <50 ng dsDNA per mg ECM dry weight; <200 bp fragment length; and lack of visible nuclear material in tissue sections stained with DAPI or H&E.

These criteria are satisfied by the decellularised tissues produced by the method of the present invention.

The remaining scaffold comprises ECM, in particular collagen. Preferably, the structure of the ECM is at least partially preserved in the scaffold and is preferably substantially preserved. Thus, the scaffold may comprise collagen fibres displaying original fibre architecture and molecular ultrastructure of the natural tissue material from which it is derived. The natural three-dimensional structures of these fibrous tissue proteins are preferably substantially retained, though some loosening or unfolding is acceptable without affecting the structural integrity of the scaffold.

It is known that cellular components specific for the scaffold's origin and/or the place of its implantation will invoke proper constructive remodelling of the ECM only when the polymeric architecture of the fibres within the decellularised tissues or organs remains at least partially intact. Therefore, ECM is better suited than any synthetic matrix to elicit functional regenerative remodelling, and provide a successful scaffold for tissue growth.

Preservation of functional ECM proteins is also important for maintenance of the biological activity, structural integrity, durability and physic-chemical properties of the scaffold. Maintenance and preservation of the hierarchy of structure from the molecular structure of proteins and glycosaminoglycans (GAGs) through to macroscopic ultrastructure of the tissue is important for the inherent physico-mechanical properties with in turn are important for tissue function. Preservation of the three-dimensional structures during decellularisation and tissue processing also improves the ultimate cellular repopulation of the tissue and regeneration of cellular and tissue-specific function.

The present invention preferably preserves ECM-derived/located GAGs while substantially removing cell-associated GAGs. Thus the process of decellularisation generally results in a reduction of total GAGs, while the ECM-associated GAGs are preferably largely preserved. This is important, as there is "cross-talk" between ECM GAGs and different cell types, helping to direct cell trafficking and cell differentiation. The ECM GAGs also serve as a store or sink for growth factors, which helps to direct tissue regeneration after implantation of the scaffold/implant.

The perfusion step or steps may be performed using an apparatus comprising a vacuum pump or a pump apparatus connected to a vacuum-generating device. The apparatus may comprise a perfusion circuit, which may include tubes, hoses, pipes or the like, for example, arranged to deliver the decellularising medium, and which may also be used to deliver any washing medium in embodiments of the method of the invention which include one or more washing steps.

An incubation chamber may be provided for housing the tissue and the decellularising medium may be pumped through the incubation chamber.

According to a third aspect of the invention there is provided an implant produced according to the first or second aspect of the invention, or to any process described herein.

According to a fourth aspect of the invention there is provided a method of producing an implant according to the first or second aspect of the invention, using an apparatus as described hereinabove.

According to a fifth aspect of the invention there is provided a method of treatment comprising surgically implanting into a patient an implant as described herein.

According to a sixth aspect of the invention there is provided the use in surgery of an implant described herein.

According to a seventh aspect of the invention there is provided an implant described herein for use in surgery.

According to a eighth aspect of the invention there is provided the use of an implant described herein in the manufacture of a product for surgery.

DETAILED DESCRIPTION OF THE INVENTION

In order that the invention may be more clearly understood an embodiments thereof will now be described, by way of example only, with reference to the accompanying drawings, of which:

FIG. 1 is a photograph which shows the macroscopic appearance of (A) control (non-decellularised) and (B) decellularised piece of human trachea using the methods of the invention;

FIG. 2 is a photomicrograph showing a histological evaluation of decellularised porcine trachea with and without the use of a vacuum during the decellularisation process, in which images A & D show normal control tissue showing the presence of intact cells with nuclei (*), B & E show tissue decellularised without the use of negative pressure during perfusion (note the intact chondrocytes within the cartilaginous lacunae (*)), and C & F show decellularisation using the methods of the invention (no intact nuclei are present, and cartilaginous lacunae are empty (°));

Figure 5:
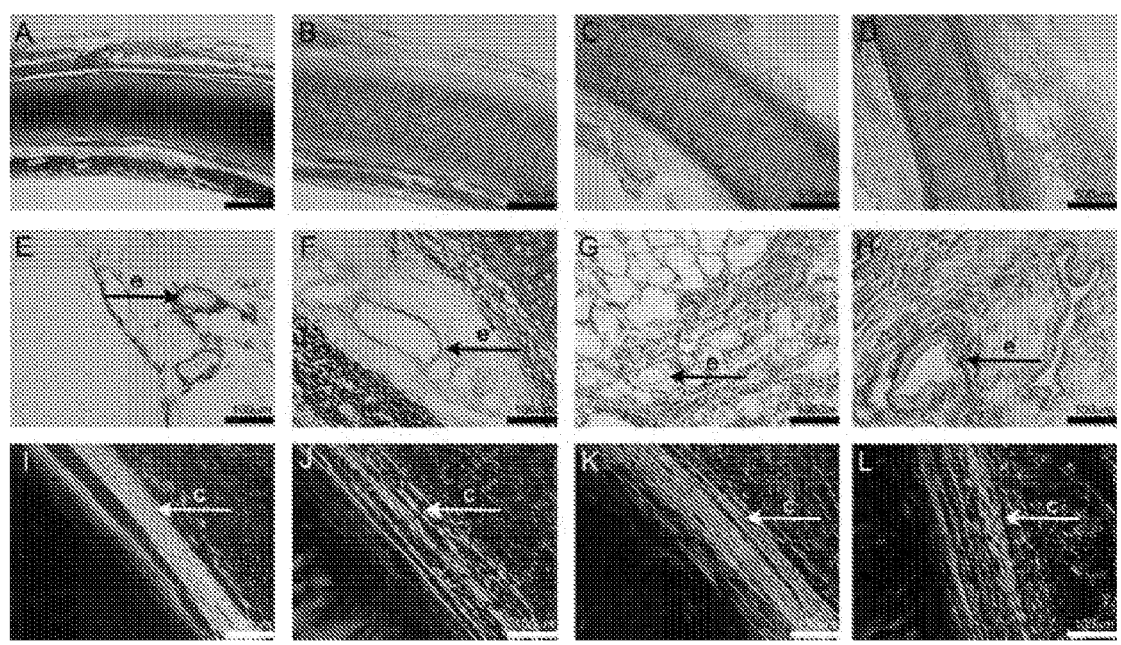
Figure 6:
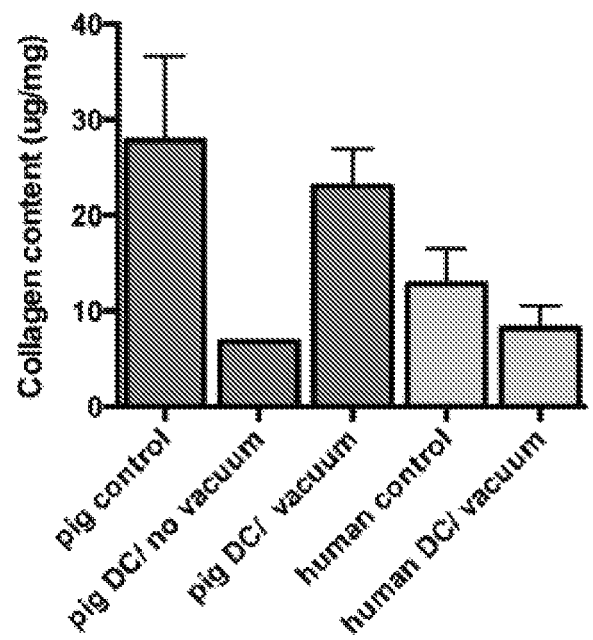
Figure 7:
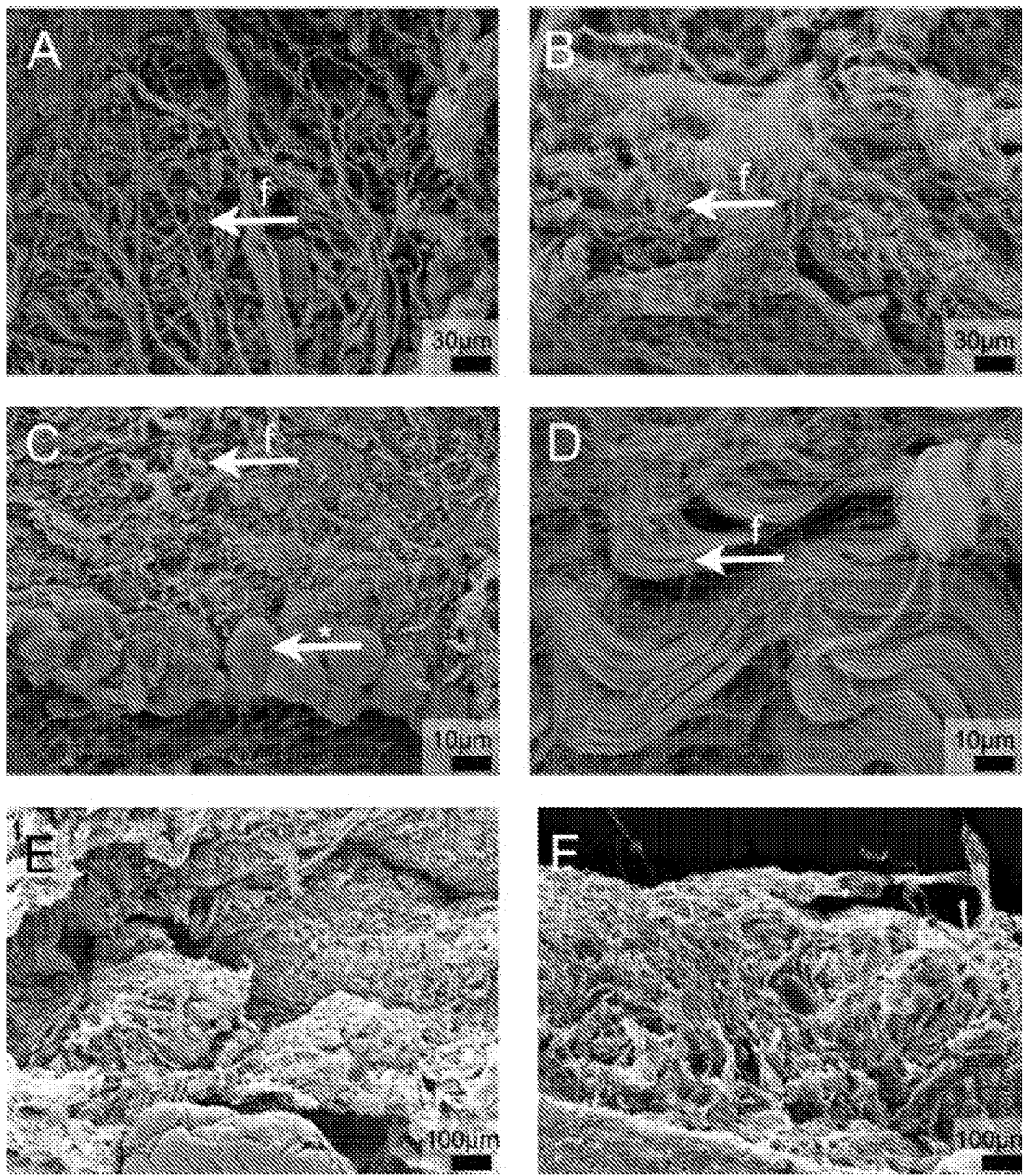
Figure 8:
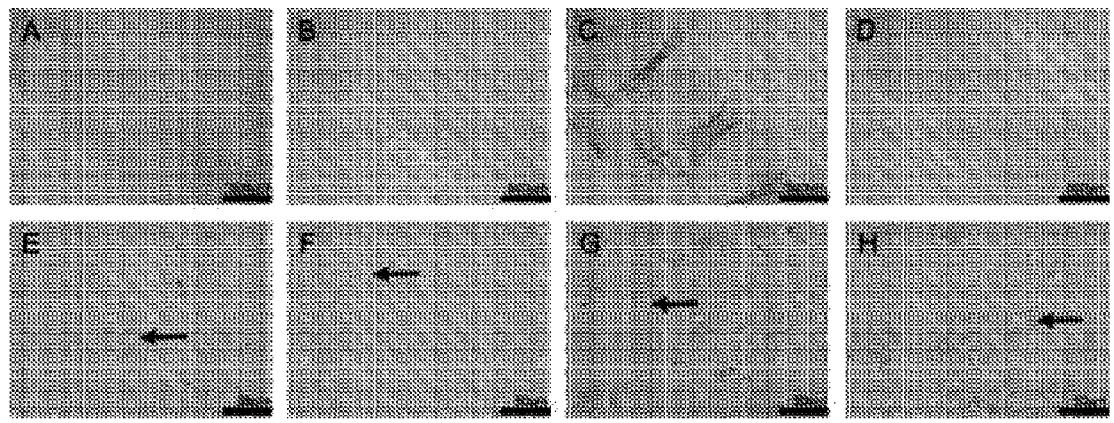
Figure 9:
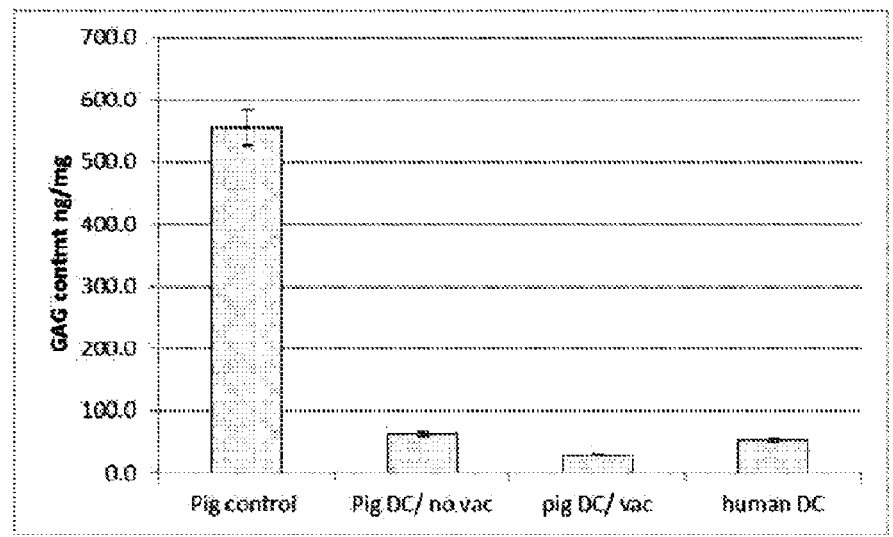
Figure 10:
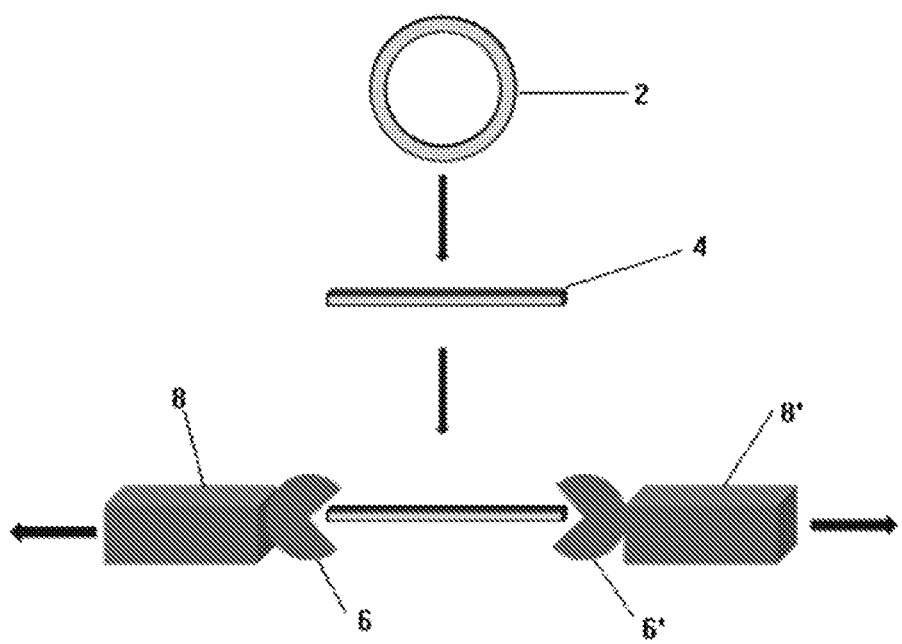
Figure 11:
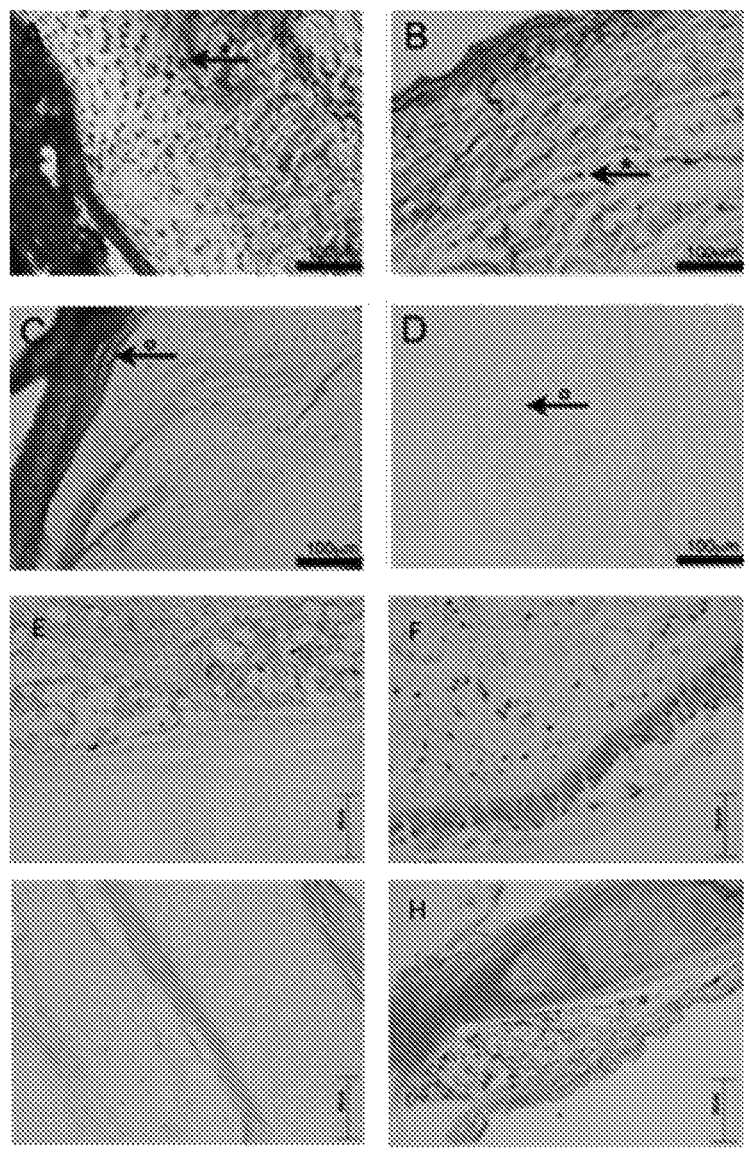
Figure 12:
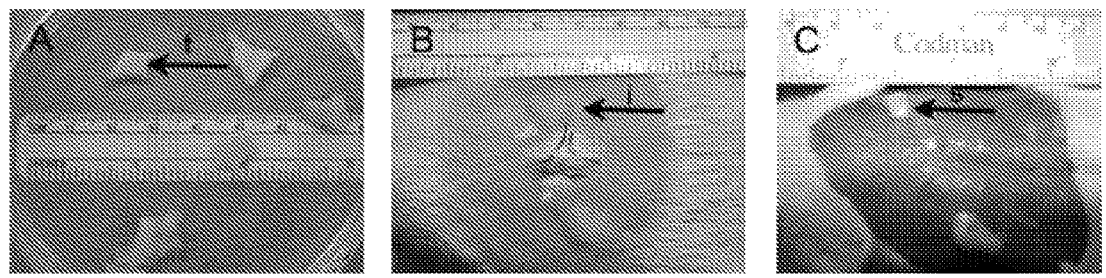
Figure 13:
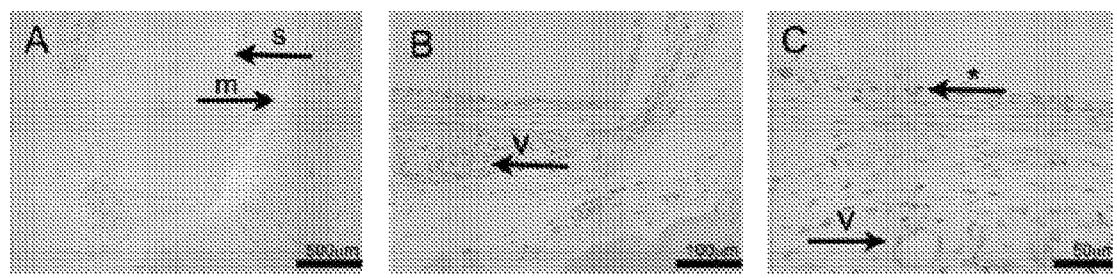
Figure 14:
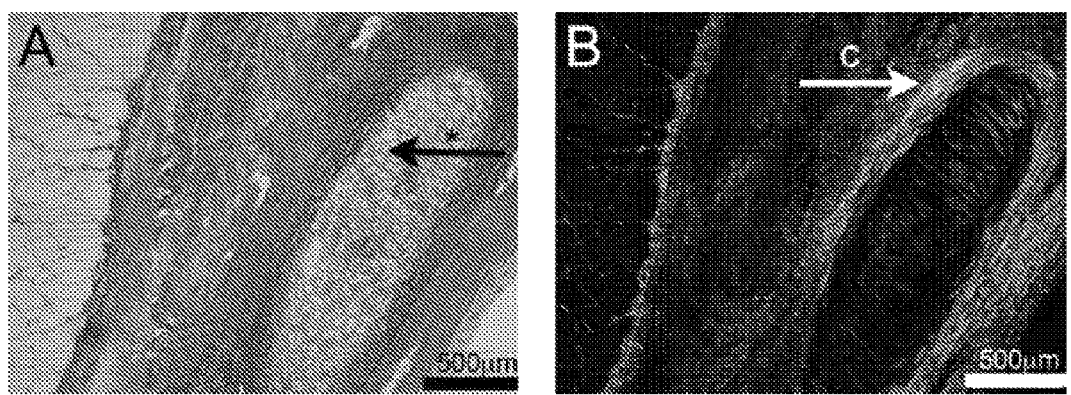
Figure 15:
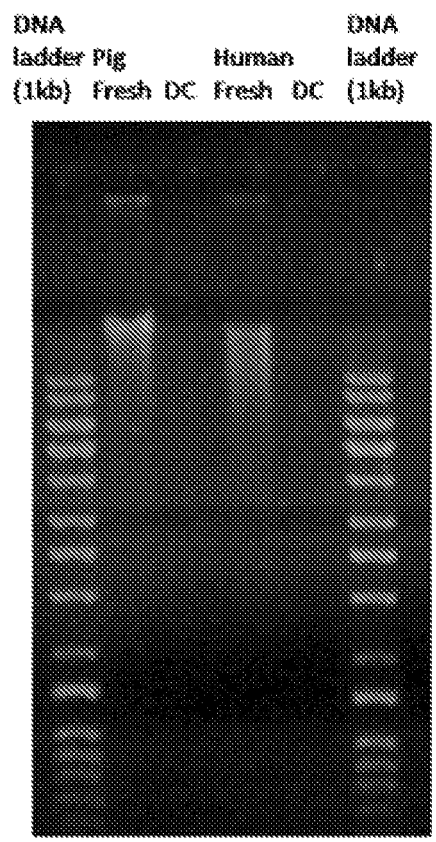
Figure 16:
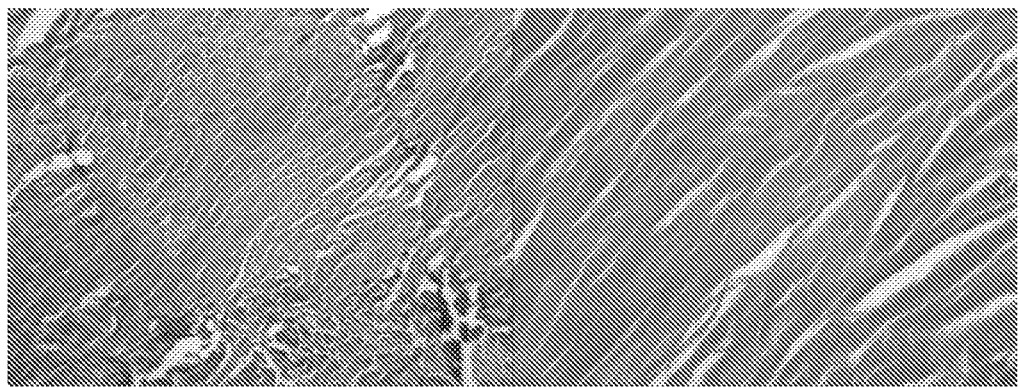
Figure 17:
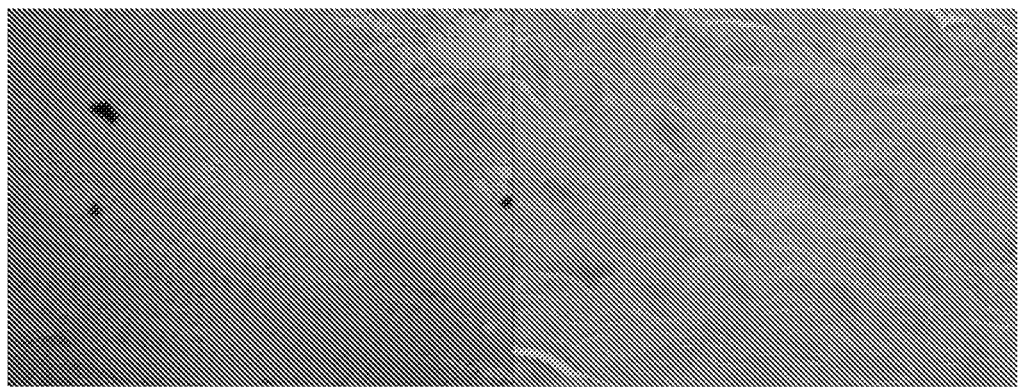
Figure 18:
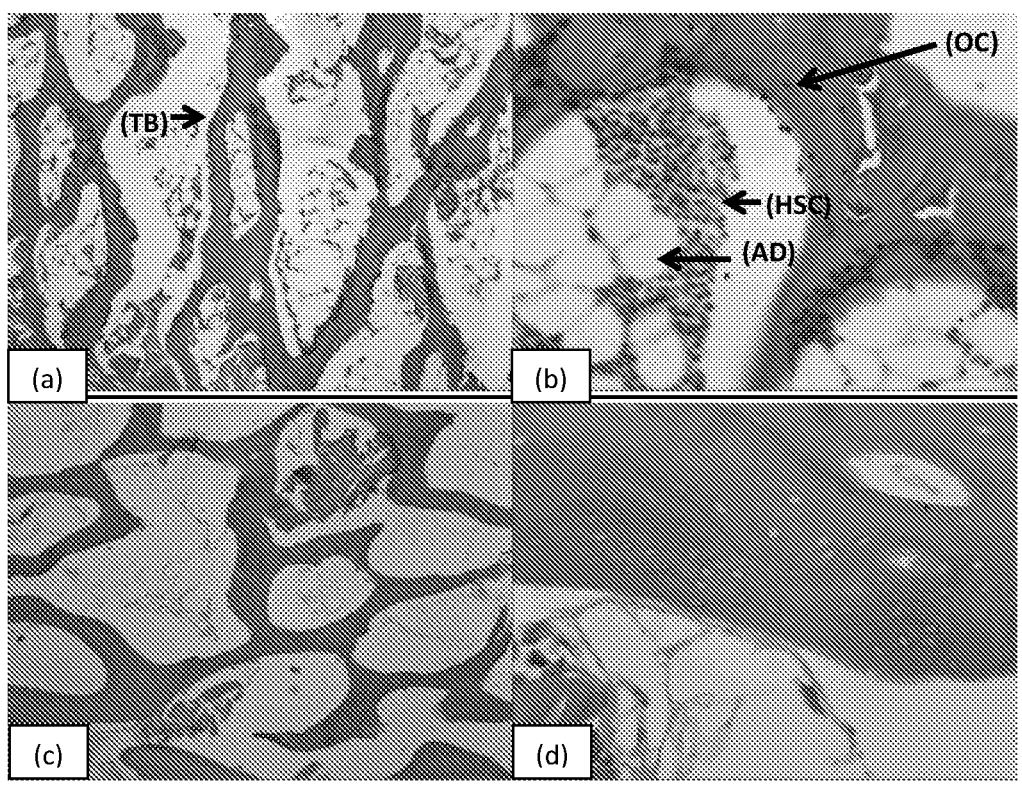

FIG. 5 is a photomicrograph showing PSR-ME elastin stained sections, in which images A to H are images of porcine (A&B, E&F) and human (C&D, G&H) tracheal tissue taken under bright field microscopic light, I to L (I&J porcine, K&L human) are taken under polarised light, and wherein control tissue in images A&E&I, C&G&K is compared to decellularised tissue prepared by the methods of the invention in images B&F&J, D&H&L. Arrows mark show conserved elastic fibres (e) and collagen fibres (c);

FIG. 6 is a bar chart showing the results of collagen content of control tissue and decellularised tissue of porcine and human trachea. For porcine tissue initial data for decellularisation without vacuum (n=2) is included. Both species show no significant difference between control tissue and decellularised tracheal samples;

FIG. 7: is a series of SEM images of tracheal tissue in which A, C, E are control tissue, and images B, D, F show decellularised trachea tissue prepared using the methods of the invention. Collagen bundles, A-D is pig and E and F are human Trachea. Arrows labelled "*" show cells in the control tissue (image C). Arrows labelled "f" are pointing towards collagen fibres;

FIG. 8 is a photomicrograph of an Alcian Blue stain of control tissue of porcine trachea (A&E), control tissue of human trachea (C&G) compared with decellularised pig (B&F) and human trachea (D&H) made according to the invention;

FIG. 9 is a bar chart showing the quantitative GAG analysis of pig and human tissue comparing control tissue and decellularised (made with and without using the methods of the invention) tissue samples;

FIG. 10 is an schematic illustration of an apparatus for the biomechanical testing of tracheal samples;

FIG. 11 is a photomicrograph showing images of immunostaining for MHC-I of porcine control (A) and decellularised (C) trachea made according to the invention and human control (B) and decellularised (D) tracheal tissue made according to the invention. Arrows labelled "*" show positive staining of the cell membranes, and arrows labelled "o" mark the area where a MHC-I stain would have been expected in case of positive staining. Non-decellularised human trachea stained with HLA-1 are shown in (E). Non-decellularised human trachea stained with HLA-1 are shown in (F). HLA-1 positive staining can be seen throughout the section; the epithelium shows intense positivity. (G) shows HLA-1 staining of decellularised human trachea made according to the invention (counter stained with eosin) showing no positivity on the cartilage and collagen. (H) shows decellularised human trachea IHC stained with HLA-1 overnight and counter stained with Eosin;

FIG. 12: is a series of photographs showing macroscopic images of a biocompatibility experiment. Image A, arrow "t", shows implantation of human decellularised tracheal samples made according to the invention in Sprague Dawley rats. Image B shows the implantation area, (note Arrow "I") and image C, Arrow "s" shows tissue samples explanted after 2 weeks;

FIG. 13: is photomicrograph of an H&E stain of explanted human decellularised tracheal tissue made according to the invention after 2 weeks of implantation in xenogenic animal model. Picture A includes arrows which indicate underlying muscle (m) and the implanted scaffold (s). B&C show images after explanation and the area shows integration of the tissue with neovascularization (v) and a thin fibrous capsule with some neutrophilic cells (*) corresponding to a mild acute inflammation;

FIG. 14 is a photomicrograph of PSR-ME stained images of decellularised human tracheal scaffolds made according to the invention after 2 weeks of implantation into rats. Arrows show the preserved extracellular matrix structure of the scaffold with the cartilaginous part (*) and the collagenous fibres (c);

FIG. 15 is a DNA gel electrophoresis showing the DNA content of samples of decellularised pig and human tracheal tissue prepared according to the invention compared to control markers of up to 1 kba;

FIG. 16 is photomicrograph of an H&E stain of porcine decellularised tendon tissue made according to the invention;

FIG. 17 is photomicrograph of an H&E stain of a control porcine decellularised tendon tissue made without the use of negative pressure during decellularisation; and FIG. 18 is a photomicrograph of H&E stained porcine bone samples. (a) Control sample (no negative pressure during decellularisation), magnification ×40. (b) Control sample, magnification ×200. (c) 1% SDS, 36 hr hypotonic solution, vacuum sample, magnification ×40. (d) 1% SDS, 36 hr hypotonic solution, vacuum sample, magnification ×200. Key—(AD) Adipocyte; (HSC) Haematopoietic stem cells. (OC); Osteocyte within lacunae of trabecular bone; (TB) Pink stained trabecular bone.

EXAMPLES

Example 1

Production of a Decellularised Tracheal Scaffold According to the Invention, and Controls All animal surgery and handling was performed in accordance with the United Kingdom Home Office Animals (Scientific Procedures) Act of 1986 following ethical approval from Northwick Park Institute for Medical Research (NPIMR). Tracheae were harvested from Large-White/Landrace crossbreed pigs from unrelated studies under standard laboratory conditions. After euthanasia by anaesthetic overdose, the tracheae were harvested and used either fresh (control) or decellularised. For decellularisation all connective tissue was removed and the trachea rinsed in Hanks balanced salt solution (Sigma-Aldrich). The tissue was then stored at −20° C. for a minimum of 24 hours. Human tracheae were obtained from NHS Blood and Transplant (NHSBT). Cadaveric tracheas were retrieved from 2 donors who had no known airway disease. The initial transfer and storage was done in Hank's Buffered Solution at −80° C. For decellularisation both tracheas were then transferred to −20° C.

Decellularisation According to the Invention, and Control Decellularisation

A total eleven (11) porcine trachea were decellularised; seven (7) were decellularised using the methods of the invention whilst four (4) were decellularised using exactly the same decellularisation protocol but under normal atmospheric pressure rather than negative pressure. Both human tracheas were decellularised using the methods of the invention. For each decellularisation process a maximum length of 5 cm of trachea was used.

The entire decellularisation process was carried out using a small desiccator (Sigma Aldrich UK). In order to create a vacuum (negative pressure), the desiccator was attached to a Telstar Vacuum Pump 2F-10 (Pendle Refrigeration Wholesale Ltd, UK) fitted with a digital vacuum gauge (Pendle Refrigeration Wholesale Ltd, UK). A vacuum was created to a level of 1500 microns (read off the vacuum gauge 1500 microns equates to <1 KPa abs). The desiccator was then placed into a shaking incubator (set 100 rpm) at either 4° C. or 37° C. depending upon the temperature required within the protocol. All solutions used during the decellularisation process contained 1% Penicillin/Streptomycin (Sigma-Aldrich, UK).

Tissue was thawed to room temperature for 1-2 hours and then incubated in a detergent solution containing 0.25% Triton X-100 (Sigma-Aldrich, UK), 0.25% Sodium Deoxycholate (Fluka) in PBS at 37° C. for 24 hours. The tissue was then rinsed twice with Hanks balanced salt solution at 4°-6° C. for 15 minutes. After washing, the tissue was incubated with Hanks balanced salt solution for 24 hrs at 4°-6° C. followed by incubation with 2000 KU (Kunitz Units)/l DNAse (Sigma-Aldrich) and 0.1 g/l RNAse (Roche) at 37° C. for 24 hours, to solubilize nuclear contents and degrade DNA. After a further rinsing (twice) with Hanks balanced salt solution at 4°-6° C. the tracheas were incubated for 24 hours of washing with Hanks balanced salt solution at 4° C. The tracheas were then either stored in Hanks balanced salt solution containing 1% antibiotic and antimycotic solution at 4°-6° C. or processed as required for further analysis. The total decellularisation process was undertaken under negative pressure and took between 4-5 days, which is a substantially shorter length of time than using known decellularisation techniques.

Implant/Scaffold Analysis
Histological and Immuno-Histochemical Evaluation:

Samples were fixed for a minimum of 24 hours in 10% neutral buffered formalin solution at room temperature. They were dehydrated in graded alcohol, embedded in paraffin and sectioned at 5 μm. Sections were stained with Haematoxylin and eosin stain (H&E), Alcian blue, Picrosirius red and Miller's elastin stains.

For immuno-histochemical analysis both paraffin and frozen sections were trialled for MHC-I immuno-staining embedded The 5 μm paraffin sections were mounted on slides coated with (3-aminopropyl) triethoxysilane (Sigma-Aldrich UK). Fresh frozen sections were fixed with ice-cold acetone for 10 minutes. Paraffin sections were de-waxed and rehydrated with two changes of xylene followed by a rinse in decreasing alcohol gradient and rinsed in cold tap water. The slides were placed in a humidification chamber and endogenous peroxidase was blocked using 3% hydrogen peroxidase in methanol (Sigma-Aldrich-Uk) for 30 minutes at room temperature. For the paraffin sections, antigen retrieval was carried out using Trypsin at 37° C. for 40 minutes. Non-specific binding sites were blocked with 2.5% horse serum (Vector Laboratories Ltd., Peterborough, UK) at room temperature for 30 minutes. Human tissue sections were subjected to incubation with the monoclonal primary antibody (anti-human MHC class I antibody produced in rabbit/EP1395Y, ab52922, Abcam, UK) for 1 hour at room temperature at 1:150 dilution in phosphate-buffered saline solution. The porcine tissue sections were incubated with the primary antibody (anti porcine MHCI, H17A, VMRD Inc. Pullman USA) at 4° C. overnight at 1:100 dilution in phosphate-buffered saline solution.

After 3×3 minute washes with PBS the sections were incubated with the secondary antibody (Impress anti-mouse or Impress anti-rabbit immunoglobulin G/peroxidase kit, Vector Laboratories) for 30 minutes at room temperature. After washing again with a 3×3 minute PBS, the chromogenic substrate diaminobenzidine (Impact peroxidase substrate, Vector Laboratories) was applied to the sections for 3 minutes at room temperature. After washing the sections were counterstained in Harris's haematoxylin for 30 seconds before dehydrating, clearing, applying a cover slip. For negative controls the same protocol was applied, however the primary antibody was omitted and phosphate-buffered saline solution was used. As a positive control pig or human spleen was used.

Scanning Electron Microscopy (SEM)

To qualitatively evaluate the decellularised matrix structure, tissue samples were fixed with 3% (v/v) glutaraldehyde (Sigma-Aldrich in) 0.1M phosphate buffer.

The fragments were then washed with distilled water and dehydrated in an ethanol gradient and dried at critical point. The specimens were then mounted on double-sided adhesive tape affixed to a scanning electron microscopy stub, and coated with gold alloy before photographs were taken.

Molecular Analysis
DNA Analysis:

For the DNA extraction and quantification the GenElute mammalian genomic DNA miniprep kit (Sigma-Aldrich—UK) was used following the manufacturer's instructions. In brief, 25 mg of minced wet tissue of fresh or decellularised tracheal tissue (human and porcine) was placed in a microcentrifuge tube with proteinase K and incubated in a water bath at 55° C. for 4 hours with vortexing at 30-minutes intervals. Complete digestion was confirmed macroscopically and the samples were then subjected to a ribonuclease A solution at room temperature for 2 minutes. The samples were incubated with lysic reagents from the DNA extraction assay kit at 70° C. for 10 minutes. The lysates were loaded into prepared columns for binding DNA. After several washing steps to remove contaminates the DNA was finally eluted in 200 μl of a Tris-ethyledeiaminetetraacetic acid solution. The absorbance was read at 260 nm and 280 nm using a self-masking quartz microcuvette and a spectrophotometer (Helios Alpha, Thermo Fisher Scientific, Loughborough, UK) and the absolute amount of DNA per milligram of tissue was calculated.

The size, quality and purity of the extracted DNA were determined by performing DNA 0.8% agarose gel electrophoresis. The 0.8% agarose gel was running in 0.5× Tris-borate-ethylenediaminetetraacetic acid buffer at 4 to 5 V/cm between the electrodes. Equal volumes of DNA (2 μl) were loaded into each well. Visualization was achieved by staining with ethidium bromide and DNA was measured via ultraviolet transillumination against a 1-kb DNA ladder (Q-Step 4 quantitative DNA ladder, Yorkshire Bioscience Ltd., York, UK).

Gag Quantification:

The Blyscan GAG assay kit (Biocolor) was used to quantify sulfated glycosaminoglycan (sGAG) content of fresh and decellularised human and porcine tracheal samples. In brief, 50 mg of minced wet tissue was placed in a micro-centrifuge tube and incubated with 1 ml of papain digestion buffer at 65° C. for 18 hours. Aliquots of each sample were mixed with 1,9-dimethyl-methylene blue dye and reagents from the GAG assay kit. The absorbance at 656 nm was measured with a spectrophotometer and the absolute GAG content calculated by comparing to a plot of standards made from bovine tracheal chondroitin-4-sulfate.

Collagen Quantification:

The collagen content of fresh and de-cellularised human and porcine trachea was quantified with the Sircol collagen assay kit (Biocolor, Carrickfergus, Northern Ireland). In brief, 50 mg of minced wet tissue was placed in a microcentrifuge tube with 1.5 ml acid-pepsin extraction medium (0.1 mg/ml pepsin in 0.5 mol/l acetic acid). Aliquots of each sample were incubated with acid-neutralizing reagent and collagen isolation reagents overnight at 4° C. Samples were then subjected to the Sirius red dye from the collagen assay kit. The absorbance at 555 nm was measured with a spectrophotometer. By comparing to a plot of standards made from type I bovine skin collagen the absolute collagen content was calculated.

Biomechanical Testing

The specimens were subjected to uniaxial tension until failure, confirmed by the loss of load and the appearance of tears in the tissue. The process is shown in the schematic of FIG. 10.

For each test one open tracheal ring (pig or human, fresh or decellularised) was used. Specimens of trachea (2) were opened to form flat rectangular pieces (4) with a maximum length of 33 mm were clamped in clamps (6,6') held in holders (8, 8') and loaded at a constant tension rate of 100 mm/min and a maximum force of 500N. The tests were performed with the application of uniaxial tension with an Instron In-Spec 2200 Benchtop Portable Tester at room temperature.

The tensile tester recorded in real-time the load and the elongation to which the tissue was subjected. Parameters such as maximum force (N), rupture force (N), extension at maximum load (cm) were recorded. The ratio of stress to strain was calculated (Young's modulus) with is a measure of the stiffness of an elastic material Biocompatibility of Decellularised Scaffold All surgery and animal handling were performed in accordance with The Animals (Scientific Procedures) Act 1986 and Home Office Code of Practice. Relevant ethics approval was sought and granted by Northwick Park Institute for Medical Research.

Prior to implantation each scaffold was sterilised further using UV sterilisation; samples were exposed to UV light for a period of 2×20 min. A total of 6 Sprague-Dawley rats were used. Under general anaesthesia and using aseptic techniques a midline incision on the abdominal wall was made and a small pocket between the skin and muscle created on both sides of the midline. Each pocket then received either a 1 cm×1 cm of decellularised or non-decellularised piece of trachea. Two weeks later each animal was terminated by a lethal dose of penotbarbitone. The implanted tissue was explanted and processed for histological evaluation.

Statistical Analysis

Data were calculated as mean+/−standard error, and significance was determined by performing 2-tailed Student's t-tests and Ordinary one-way-ANOVA with Bonferroni as a post-hoc test (Prism 6: Graphpad Software, La Jolla, Calif.). A p value of less than 0.05 was considered to be significant.

Results

Tracheal tissue was harvested from 11 pigs and 2 human donors and treated with the decellularisation (hereinafter "DC") process according to the invention.

Figure 1:
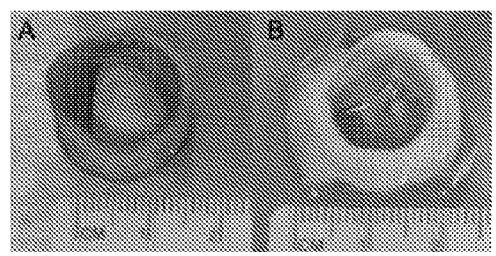

DNA Analysis:

Following decellularisation macroscopically the tissue appears colourless, probably due to the removal of red blood cells (see FIG. 1).

Figure 2:
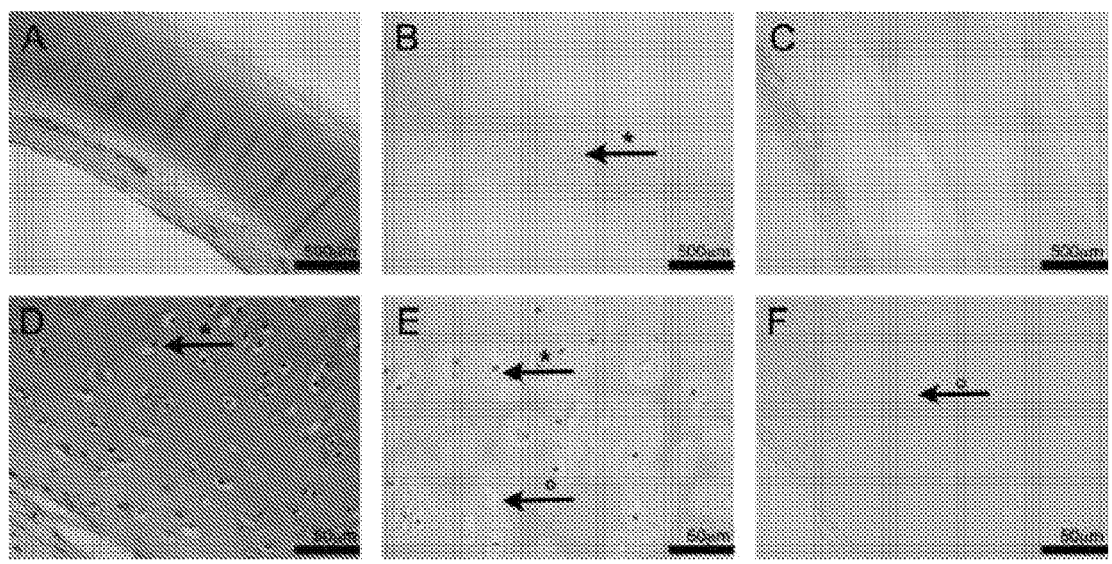

Porcine tracheas were decellularised with and without vacuum to assist the penetration of the solutions into the tissue. On histological H&E stained slides, there was complete clearance of all intact nuclei within luminal epithelium (mucosa), sub-mucosal glands, the trachealis muscle and the outer adventitia in tissue which had been subjected to vacuum assisted decellularisation, which is the method according to the invention. Within the cartilage, all chondrocytes were efficiently removed from within lacunae. However, tissue that had not been subjected to vacuum assisted decellularisation showed intact chondrocytes within some, but not all, lacunae (FIG. 2). This observation was supported by the molecular DNA quantification which showed a significant reduction in the amount of DNA left behind after decellularisation with and without vacuum when compared with the control tissue. Furthermore, a non-significant reduction in DNA was observed between the non-vacuum and vacuum assisted protocol (FIG. 3: control n=7, 300.4±27.05 ng/mg vs. DC no-vac: n=3, 109.8±37.45 ng/mg vs. DC vac n=6, 36.14±7.834 ng/mg, p<0.05.)

Figure 3:
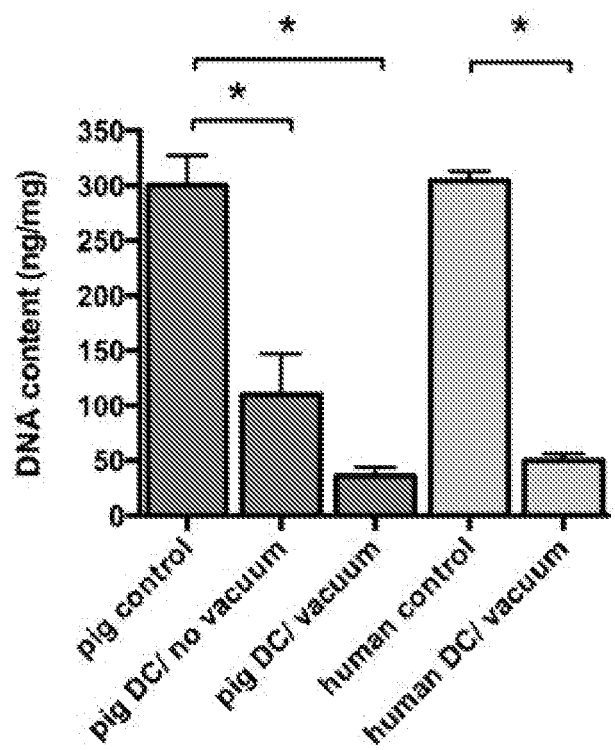
FIG. 3 shows a bar graph of the results of DNA quantification in control porcine tissue and porcine tissue decellularised with and without the use of the methods of the invention, and DNA quantification for human tracheal control tissue and tissue decellularised using the methods of the invention.
Figure 4:
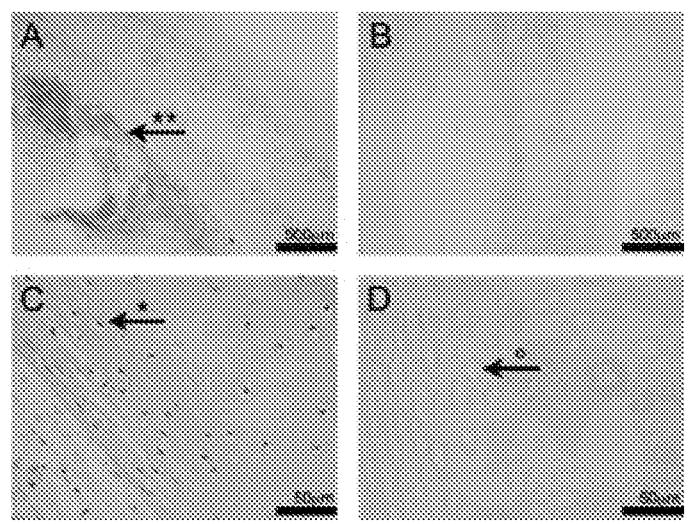
FIG. 4 is a photomicrograph showing the decellularisation of human trachea using the methods of the invention, in which images A&C show normal control tissue (note the intact chondrocytes (*) and the nuclear material in the outer connective tissue (**)) and B&C show decellularised tissue prepared using the methods of the invention (note empty cartilaginous lacunae (°))

The human tracheas which had all been subjected to vacuum de-cellularisation also showed complete clearance of all nuclear material throughout the tissue both histologically (FIG. 4) and with molecular DNA analysis (control n=2, 304.4±8.268 ng/mg vs. DC n=7, 50.04±6.003 ng/mg, p<0.05 see FIG. 3). FIG. 15 also indicates removal of substantially all DNA.

Collagen Assessment

Evaluation of tissue from both species by Picro-Sirius red with Miller elastin showed good preservation and morphology of the cartilage and collagen (FIG. 5, A-D). Additionally, the fine elastin within small arterioles and venules was also preserved (FIG. 5, E-H). When sections were viewed under polarised light (FIG. 5, I-L) all collagen bi-refringed a bright red-orange-yellow colour representing good structural integrity of the collagen.

With regards to molecular analysis for collagen degradation, there was a marked reduction between the control and non-vacuum assisted porcine samples. No reduction in collagen degradation was observed between the porcine control and samples prepared by the method of the invention, nor was any difference noted between the human decellularised tissue made according to the invention and control tissue. (pig: control n=9, 27.8±8.829 µg/mg, DC no-vac n=2, 6.774±0.067 µg/mg, DC vac: n=49, 23.03±3.897 µg/mg, human: control n=3, 12.86±3.657 µg/mg, DC n=9, 8.186±2.322 µm/mg see FIG. 6).

Collagen ultra-structure was also assessed using SEM, collagen fibre within porcine decellularised tissue made according to the invention appeared to be more loosely bound in than in the control porcine tissue. Similar appearance was also noted for human tissue (FIG. 7).

Scaffold GAG's Evaluation

Evaluation of the amount of GAG's retained on the decellularised scaffold from both species was assessed using Alcian blue histological staining (FIG. 8) and quantitative molecular testing. Whereas the pig scaffolds lost over 70% of their GAGs content during the decellularisation process with and without vacuum (control n=14, 488.3±75.61 ng/mg vs. DC no vacuum n=10, 59.12±11.54 ng/mg vs. DC vacuum n=8, 47.37±3.921, p<0.05), human tissue does not show large differences (control n=2, 44.03±0.89 vs. DC/n=7, 57.64±3.12)

Biomechanics

Biomechanical analysis of both control and decellularised (prepared according to the invention only) was also undertaken for both species, as shown in FIG. 10. The samples were prepared by taking one cartilaginous ring (2), cutting it open and removing the pars membranacea to produce a homogenous rectangular piece of tissue (4) which was then clamped between sand paper in the sample holders (8, 8'). No significant differences were noted for any of the following parameters; tensile strength, rupture force, elongation to break and Youngs modulus, the date for each is presented in Table 1.

TABLE 1

Results of biomechanical testing, comparing Tensile strength, rupture force, Elongation at break and Young's Modulus for control and decellularised tracheal tissue (using the method of the invention) from both pig and human.

|  | pig control (n = 12) | pig DC (n = 5) | significance | Human control (n = 2) | human DC (n = 3) | significance |
|---|---|---|---|---|---|---|
| Tensile strength (kPa) | 3326 +/− 292.4 | 3022 +/− 404.7 | ns (p = 0.4494) | 1240 +/− 754.8 | 1503 +/− 808.9 | ns (p = 0.4743) |
| Rupture force (N) | 33.26 +/− 2.924 | 30.22 +/− 4.047 | ns (p = 0.4494) | 12.40 +/− 7.548 | 15.03 +/− 8.089 | ns (p = 0.4743) |
| Elongation at break (%) | 79.34 +/− 5.804 | 68.57 +/− 3.805 | ns (p = 0.0555) | 43.28 +/− 22.17 | 48.48 +/− 5.696 | ns (p = 0.0864) |
| Young's Modulus (kPa) | 4587 +/− 615.9 | 4382 +/− 462.0 | ns (p = 0.0868) | 5096 +/− 4354 | 3441 +/− 1977 | ns (p = 0.2140) |

Biocompatibility

Prior to undertaking an in vivo biocompatibility study, decellularised samples from both species were IHC stained to assess if they were capable of eliciting a potential immunological response from the host when implanted. Samples were stained MHC I/HLA-1. Sections stained with MHC showed positivity in the overlaying facia/adventitia in both species. Very little to no staining was seen in the cartilaginous rings (as shown in FIG. 11). Human sections stained with MHC1/HLA-1 showed no positivity in either the cartilage, collagen or overlying facia (as shown in FIG. 11).

Small pieces of decellularised trachea were implanted subcutaneously into rats and left for 2 weeks. On explanation (as shown in FIG. 12) each implanted sample could still identified. All histological sections from the implanted DC human trachea showed minor inflammatory response—acute with a little chronic (neutrophils, eosinophils in small number, moderate amounts of macrophages with the occasional syncytia of lymphocytes), as shown in FIG. 13. Additionally, there was good neovascularisation and good integration and the extracellular matrix appeared intact, as shown in FIG. 14.

Example 2

Production of a Decellularised Bone and Tendon Scaffold According to the Invention, and Controls Tissue samples were obtained from Pigs terminated in unrelated studies. The pigs were all female, approximately 5 months in age and 50 kg weight. Samples of bone were obtained from the porcine Calcaneus. Tendon samples were obtained from the flexor digitorum longus tendon. The samples were removed during post-mortem and stored in a freezer at −20° C. in plastic sample bags until required for use in protocols.

A similar protocol to that described above for tracheal implant production was performed for producing bone and tendon implants, using SDS, TnBP (tri-n-butyl phosphate), Triton X-100, DNAse and RNAse as the decellularising agents carried out under negative pressure conditions. Control samples of bone and tendon perfused by decellularising agents without the use of negative pressure were also used and the resultant tissue were analysed histologically.

The protocol used is shown in Table 2 below and all steps were performed under negative pressure of 0.2 kPa for the tissue perfused using the methods of the invention or with ambient pressure for control tissue samples. Between each step shown in Table 2, three 15 minute washes were carried out with deionized water.

TABLE 2

Table 2 - decellularisation protocol steps for bone and tendon tissue samples.

| Step | Solution | pH | Temp. (° C.) | Time Period (Hours) |
|---|---|---|---|---|
| 1. | Hypotonic 10 mM trizma base, 0.4 mM PMSF (dissolved in 1 ml ethanol), 5 mM EDTA | 8.5 | 20 | 24 or 36 |
| 2. | Hypertonic 1.5M Potassium Chloride, 50 mM trizma base, 1% (v/v) triton x-100, 0.4 mM PMSF | 8.0 | 20 | 48 |
| 3. | Deionized water | 7.0 | 37 | 24 |
| 4. | PBS, DNase, 0.04 mgml$^{-1}$ RNase | 7.6 | 37 | 5 |
| 5. | 50 mM trizma base with either 1% (w/v) SDS or 1% (v/v) TnBP (tri-n-butyl phosphate) | 8.0 |  | 72 120 168 216 and 264 |
| 6. | 50 mM trizma base | 9.0 | 20 | 24 |
| 7. | PBS | 8.0 | 20 | 24 |

After decellularisation, Haematoxylin and Eosin (H&E) staining was carried out in order to establish the presence of any remaining nuclear material. Picro-Sirius Red and Miller's Elastin (P&M) staining was carried out in order to assess the condition of the collagen and elastin fibres within the ECM. Representative photographs were taken of all the samples through a light microscope at ×40 and ×200 magnification. All the P&M slides were photographed through unpolarised and polarised light to help emphasise the condition of the collagen and elastin fibres. FIGS. 16 & 17 show the results of the H&E staining of tendon tissue prepared according to the invention (FIG. 16) and control tendon tissue (FIG. 17). FIG. 18 shows the results of the H&E staining of bone tissue according to the invention.

Full decellularisation with elimination of nuclear material from tendon tissue was achieved under negative pressure conditions (FIG. 16) according to the methods of the invention, while nuclear material was still visible in the control tendon samples prepared under ambient pressure (FIG. 17). Likewise, bone tissue samples prepared according to the invention under negative pressure de-cellularisation were found to have substantially no nuclear material present, leaving visibly empty lacunae, as shown in the H&E stained samples of FIG. 18.

Example 3

Production of a Decellularised Larynx According to the Invention

Tissue samples were obtained from human cadavers and stored at −20° C. in plastic bags.

A similar protocol to that described in Example 1 was performed for the larynx samples using DNAse, RNAse, Triton X-100 and sodium deoxycholate (SOC) as the decellularisation agents. All of the steps of the method were carried out under negative pressure conditions of <1 kPa using a desiccator and Telstar Vacuum Pump 2F-10 as described for Example 1, at 1500 microns.

The components of the protocol are described below and the protocol shown in Table 3 below:

Solution Preparation latrunculin B (Lat B) powder form—1 mg Lat B 395.51 g/mol.

To this was added 25 ml of High glucose DMEM which produced a 100 µM stock solution, aliquoted into 25 1 ml tubes and stored in a −20° C. freezer.

1. 50 nM latrunculin B (Lat B) in high glucose DMEM (4500 mg glucose)—50 µl of Lat B in 100 ml of high glucose DMEM (Dulbecco's Modified Eagle Medium).
2. 0.25% Triton X & 0.25% SOC—To 1 liter of PBS was added 2.5 g of Sodium Deoxycholate Solution (SOC) and 2.5 ml of Triton X.
3. PBS −5 PBS tablets were added to 1 liter of deionised water.
4. Hanks balanced salt solution with added calcium and magnesium—from Sigma Aldrich H6648.
5. 0.6M Potassium Chloride (KCl)—to 1 liter of PBS was added 44.73 g of KCl
6. 1M Potassium Iodide (KI)—to 1 liter of PBS was added 166 g of KI
7. Incubation Buffer—to 1 liter of PBS were added—0.5 g of Magnesium chloride (MgCl$_2$), 0.055 g of calcium chloride (CaCl$_2$), DNAse was added to the required volume of incubation buffer immediately before use.
8. DNAse—1 vial of DNAse containing 2000 ku of enzyme, was mixed into 1 liter of deionised water. 5 ml of water was placed into a vial of DNAse and aliquoted into 5, 1 ml Eppdorff tube. 1 ml of the prepared enzyme solution was used for 200 ml of incubation buffer.
9. RNAse—100 ml of incubation buffer was mixed with 0.01 g of RNAse.

TABLE 3

| Step | Reagent | Time | Step performed under negative pressure | Temp (° C.) |
|---|---|---|---|---|
| 1 | Latrinculin B | 2 h | ✓ | 37 |
| 2 | Hanks balanced salt solution (HBSS) | 2 × 15 min | ✓ | RT |
| 3 | KCL | 2 h | ✓ | RT |
| 4 | Hanks balanced salt solution | 2 × 15 min | ✓ | RT |
| 5 | KI | 2 h | ✓ | RT |
| 6 | Hanks balanced salt solution | Over night | ✓ | RT |
| 7 | KCL | 2 h | ✓ | RT |
| 8 | Hanks balanced salt solution | 2 × 15 min | ✓ | RT |
| 9 | KI | 2 h | ✓ | RT |
| 10 | Hanks balanced salt solution | 2 × 15 min | ✓ | RT |
| 11 | DNAse/RNAse | 2 h | ✓ | 37 |
| 12 | Hanks balanced salt solution | 2 × 15 min | ✓ | RT |
| 13 | Freeze | 12 h +/− 4 h | ✓ | −20 |
| 14 | Thaw | 12 h +/− 4 h | ✓ | RT |
| 15 | Triton/SOC | 24 h | ✓ | RT |
| 16 | Hanks balanced salt solution | 2 × 15 min | ✓ | RT |
| 17 | DNAse/RNAse | 24 h +/− 4 h | ✓ | 37 |
| 18 | Hanks balanced salt solution | 2 × 15 min | ✓ | RT |
| 19 | Triton/SOC | 1 h | ✓ | RT |
| 20 | Hanks balanced salt solution | 2 × 15 min | ✓ | RT |
| 21 | Hanks balanced salt solution | 48-72 hr | ✓ | 4 |

The results of the protocol produced decellularised larynx tissue with full decellularisation and elimination of nuclear material.

The above embodiments are described by way of example only. Many variations are possible without departing from the scope of the invention as defined in the appended claims.

The invention claimed is:

1. A method for producing an implant from interstitial, connective or supporting tissue, the method comprising
   at least one step of perfusing the tissue with at least one decellularization medium; and
   a washing step after the at least one perfusion step, wherein the entire method is performed under application of only negative pressure of no more than 5 kPa.

2. A method as claimed in claim 1, wherein the at least one decellularization medium comprises a detergent and/or an enzyme.

3. A method as claimed in claim 2, wherein the method comprises at least one step of perfusion comprising a detergent decellularization medium, and at least one step of perfusion comprising a nuclease decellularization medium.

4. A method as claimed in claim 1, comprising multiple perfusion steps, and comprising a washing step between each perfusion step, and a washing step after the last perfusion step.

5. A method as claimed in claim 1, comprising a first perfusion step comprising a detergent decellularization medium, a second perfusion step comprising a nuclease decellularization medium, and a third perfusion step comprising a nuclease decellularization medium.

6. A method as claimed in claim 1, wherein the at least one perfusion step is performed at a temperature of between 25° C. and 40° C.

7. A method as claimed in claim 1, wherein each perfusion step is carried out for between 1 hour and 96 hours.

8. A method as claimed in claim 1 wherein each perfusion step, or the entire method, is performed at no more than 1 kPa.

9. A method as claimed in claim 1 wherein each perfusion step, or the entire method, is performed at no more than 0.1 kPa.

10. A method as claimed in claim 1, wherein each perfusion step comprises pumping of the decellularisation medium with a pump.

11. A method as claimed in claim 10, wherein the pump is connected to a vacuum-generating apparatus, or is a vacuum pump.

12. A method as claimed in claim 1, wherein the method further comprises the step of re-seeding the implant with cells.

13. A method as claimed in claim 12, wherein the cells comprise autologous cells and/or allogenic cells.

14. A method as claimed in claim 1 wherein the tissue is selected from the group consisting of a trachea, a portion of a trachea, tracheal tissue, bone, tendon, ligament, bone-tendon, cartilage, larynx, a portion of a larynx, larynx tissue, a large blood vessel, a portion of a large blood vessel, and nervous tissue.

\* \* \* \* \*